United States Patent
Dec et al.

(10) Patent No.: US 7,371,239 B2
(45) Date of Patent: May 13, 2008

(54) SPINAL ROD INSERTION INSTRUMENT

(75) Inventors: Brian Dec, Lafayette Hill, PA (US); Stuart Weikel, Drexel Hill, PA (US); Ernest Corrao, Bethel, CT (US); Alan Bachman, Milford, CT (US)

(73) Assignee: Synthes (U.S.A.), West Chester, PA (US)

( * ) Notice: Subject to any disclaimer, the term of this patent is extended or adjusted under 35 U.S.C. 154(b) by 617 days.

(21) Appl. No.: 10/886,328

(22) Filed: Jul. 6, 2004

(65) Prior Publication Data

US 2006/0009775 A1    Jan. 12, 2006

(51) Int. Cl.
*A61F 2/30* (2006.01)
(52) U.S. Cl. ............................ 606/61; 606/86; 606/99; 606/103
(58) Field of Classification Search .................. 606/86, 606/99, 103; 74/424.71
See application file for complete search history.

(56) References Cited

U.S. PATENT DOCUMENTS

| | | |
|---|---|---|
| 3,604,487 A | 9/1971 | Gilbert |
| 4,050,464 A | 9/1977 | Hall |
| 4,271,836 A | 6/1981 | Bacal et al. |
| 4,347,845 A | 9/1982 | Mayfield |
| 4,409,968 A | 10/1983 | Drummond |
| 4,411,259 A | 10/1983 | Drummond |
| 4,422,451 A | 12/1983 | Kalamchi |
| 4,567,884 A | 2/1986 | Edwards |
| 5,020,519 A | 6/1991 | Hayes et al. |
| 5,060,365 A | 10/1991 | Lanzo |
| D331,625 S | 12/1992 | Price et al. |
| 5,167,662 A | 12/1992 | Hayes et al. |
| 5,190,550 A | 3/1993 | Miller et al. |
| 5,246,442 A | 9/1993 | Ashman et al. |
| 5,281,223 A | 1/1994 | Ray |

(Continued)

FOREIGN PATENT DOCUMENTS

DE          4238339        5/1994

(Continued)

*Primary Examiner*—Eduardo C. Robert
*Assistant Examiner*—Andrew Yang
(74) *Attorney, Agent, or Firm*—Stroock & Stroock & Lavan LLP

(57) ABSTRACT

A surgical instrument is provided for urging a longitudinal spinal member into a bone fastener. The surgical instrument may include a holder assembly for engaging a bone fastener, the holder assembly preferably comprising a pair of pivotably connected members arranged in a scissor type configuration, and a reducing mechanism for moving the spinal rod with respect to the bone fastener, the reducing mechanism including a rod contacting member and an outer support structure having an opening for receiving at least a portion of the holder assembly and a cavity for receiving at least a portion of the vertical drive mechanism which is sized and configured to threadably engage the holder assembly. The holder assembly preferably includes a pair of jaws each having an extension formed thereon for engaging a recess formed on the lateral side walls of the bone fastener so that the holder assembly can engage the bone fastener without extending into the U-shaped channel. More preferably, the jaws may be sized and configured to engage only one of the side walls formed on the head of the bone fastener. The surgical instrument may further include a horizontal drive mechanism for aligning a laterally offset spinal rod with respect to the bone fastener.

18 Claims, 11 Drawing Sheets

U.S. PATENT DOCUMENTS

| | | |
|---|---|---|
| 5,282,302 A | 2/1994 | Starks et al. |
| D346,217 S | 4/1994 | Sparker et al. |
| 5,364,397 A | 11/1994 | Hayes et al. |
| 5,385,565 A | 1/1995 | Ray |
| 5,430,919 A | 7/1995 | Starks et al. |
| D363,545 S | 10/1995 | Miller |
| 5,509,596 A | 4/1996 | Green et al. |
| 5,520,704 A | 5/1996 | Castro et al. |
| 5,707,371 A | 1/1998 | Metz-Stavenhagen |
| 5,720,751 A | 2/1998 | Jackson |
| 5,782,830 A | 7/1998 | Farris |
| 5,810,878 A | 9/1998 | Burel et al. |
| 5,899,901 A | 5/1999 | Middleton |
| 5,910,141 A * | 6/1999 | Morrison et al. ............. 606/61 |
| 5,941,885 A | 8/1999 | Jackson |
| 6,015,409 A | 1/2000 | Jackson |
| 6,015,413 A | 1/2000 | Faccioli et al. |
| 6,017,342 A | 1/2000 | Rinner |
| 6,036,692 A * | 3/2000 | Burel et al. .................... 606/61 |
| 6,123,707 A | 9/2000 | Wagner |
| 6,139,549 A | 10/2000 | Keller |
| 6,183,472 B1 | 2/2001 | Lutz |
| 6,440,133 B1 | 8/2002 | Beale et al. |
| 6,516,505 B1 | 2/2003 | Taylor |
| 6,517,554 B1 | 2/2003 | Zhu et al. |
| 6,530,929 B1 | 3/2003 | Justis et al. |
| 6,641,595 B1 | 11/2003 | Moran et al. |
| 6,648,888 B1 | 11/2003 | Shluzas |
| 6,660,006 B2 | 12/2003 | Markworth et al. |
| 6,660,010 B2 | 12/2003 | Gellman |
| 6,712,819 B2 | 3/2004 | Zucherman |
| 6,723,100 B2 | 4/2004 | Biedermann |
| 6,726,692 B2 | 4/2004 | Bette |
| 6,743,231 B1 | 6/2004 | Gray et al. |
| 6,746,449 B2 | 6/2004 | Jones et al. |
| 2001/0027318 A1 | 10/2001 | Oribe et al. |
| 2002/0019633 A1 | 2/2002 | Ray |
| 2002/0099377 A1 | 7/2002 | Zucherman et al. |
| 2002/0161368 A1 | 10/2002 | Foley et al. |
| 2002/0169448 A1 | 11/2002 | Vanacker |
| 2003/0009168 A1 | 1/2003 | Beale et al. |
| 2003/0018342 A1 | 1/2003 | Oribe et al. |
| 2003/0023243 A1 | 1/2003 | Biedermann et al. |
| 2003/0040746 A1 | 2/2003 | Mitchell et al. |
| 2003/0060826 A1 | 3/2003 | Foley et al. |
| 2003/0225408 A1 | 12/2003 | Nichols et al. |
| 2003/0229355 A1 | 12/2003 | Keller |
| 2004/0049191 A1 | 3/2004 | Markworth et al. |
| 2005/0245928 A1* | 11/2005 | Colleran et al. ............. 606/61 |

FOREIGN PATENT DOCUMENTS

| | | |
|---|---|---|
| DE | 19828137 | 1/2000 |
| FR | 2677242 | 12/1992 |
| FR | 2729291 | 7/1996 |
| WO | WO 9311715 | 6/1993 |
| WO | WO 9844858 | 10/1998 |
| WO | WO 3028566 | 4/2003 |

* cited by examiner

SPINAL ROD INSERTION INSTRUMENT

TECHNICAL FIELD

The present invention relates generally to surgical instruments for spinal surgery. More specifically, the present invention relates to an instrument for urging a longitudinal spinal rod into a rod-receiving channel of a vertebra engaging spinal implant.

BACKGROUND

To correct spinal deformities caused by either injury or defects in the natural formation of the spine, a spinal fixation system is typically employed in an osteosynthesis surgical procedure. A typical spinal fixation system may incorporate a plurality of bone fasteners substantially aligned along the length of the spine each interconnected by a spinal rod. The spinal rod is received in a channel formed in the head of the bone fasteners. The bone fastener may be anchored to the lamina or pedicle of the vertebral body by either a threaded shank or hook which extends from the head of the fastener. The hook-type bone fastener may, in addition, be anchored to the transverse process.

Surgeons have, however, often encountered considerable difficulty when performing this surgical procedure, due to problems associated with aligning the spinal rod(s) within the rod receiving channels formed in the heads of the bone fasteners. For example, the heads of the bone fasteners may be out of vertical and/or horizontal alignment with one another due to the curvature of the spine or the size and shape of each vertebrae. This misalignment may require that the spinal rod be bent so that it may be properly seated within the rod receiving channel. The spinal rod may additionally be bent to provide a selected configuration for correction of the spinal defect. The spinal rod may also have a straight configuration. The forced interconnection of the bone fastener via the spinal rod may transfer corrective stresses to the patient's spine.

One type of bone fastener often used in the spinal fixation system is referred to as a top loading bone fastener. More specifically, the bone fastener may include a head having a U-shaped rod-receiving channel extending therethrough and a top opening to receive a closure cap to secure the spinal rod in the U-shaped channel. The U-shaped channel communicates with the top of the head of the bone fastener and defines a passageway for receipt of the spinal rod. The head of the bone fastener itself is typically spherical or cylindrical in nature in which the external side surfaces of the wall may be arcuate in shape, although other shapes are possible.

Instruments for reducing, i.e., moving, the spinal rod into the U-shaped channel of the bone fastener are typically necessary. Often times, more than one surgical instrument is used wherein one instrument attaches to the bone fastener to either stabilize the head of the bone fastener during the rod installation procedure or to act as a guide for a second surgical instrument which introduces the spinal rod into the U-shaped rod-receiving channel. A problem with an installation procedure requiring two surgical instruments is that it does not enable a surgeon to maintain one hand free, possibly requiring multiple surgeons to complete the surgical procedure. Alternatively, when a single surgical instrument is used to provide both the stabilization of the implant and application of the necessary introductory force to the spinal rod, the surgical instrument typically engages the head of the bone fastener on both sides of the U-shaped channel and thus at least a portion of the surgical instrument straddles across the U-shaped channel. That is, generally speaking, the surgical instrument attaches in a manner that encroaches over the top opening of the U-shaped channel, severely limiting access to the open channel. In addition, a rod reducing instrument which engages the head of the bone fastener on both sides of the U-shaped channel is limited in its angle of approach with respect to the bone fastener and therein unnecessary complicates the surgical procedure especially where the geometry of the surgical area does not allow the surgeon to grasp both lateral sides of the head and install the closure cap. The surgical area may be decreased and be smaller because of the natural anatomy of the patient and by the surgical instrument that must be secured to both lateral sides of the U-shaped channel formed in the head of the bone fastener.

SUMMARY

The present invention may relate to a surgical instrument for urging a longitudinal spinal rod into a bone fastener, wherein the fastener preferably includes a head and a bone engaging portion, the head may further include a top surface, a bottom surface, two lateral side walls defining a U-shaped channel, and a top opening so that the spinal rod can being introduced into the U-shaped channel through the top opening. The side walls of the bone fastener may also include opposing end faces having a recess with a pair of end walls and a seat disposed therebetween for engaging the surgical instrument.

The surgical instrument may include a holder assembly and a reducing mechanism. The holder assembly being sized and configured to engage the bone fastener, while the reducing mechanism is sized and configured for moving the spinal rod with respect to the bone fastener. The holder assembly may comprise a pair of pivotably connected members arranged in a scissor type configuration having a first end and a second end, at least a portion of the first end includes a region having grooves and wherein the second end is sized and configured to engage the head of the bone fastener. The reducing mechanism may comprise a rod contacting member, an outer support structure, and a vertical drive mechanism, the rod contacting member having a first end and a second end, the first end being sized and configured to contact the spinal rod, the outer support structure having a first end, a second end, a drive region, and a holder region wherein the holder region includes a first opening in the first end of the support structure for receiving at least a portion of the first end of the holder assembly and the drive region includes a cavity for receiving at least a portion of the vertical drive mechanism, the vertical drive mechanism including a longitudinal member configured to engage the grooved region of the holder assembly so that movement of the vertical drive mechanism moves the reducing mechanism with respect to the holder assembly.

The grooved region may include a plurality of recesses and projections, and the longitudinal member may be at least partially threaded, the threads being sized and configured to interact with the recesses and projections.

The first pivotably connected member of the holder assembly may include a grooved region having a plurality of recesses and projections formed thereon, and the second pivotably connected member may also include a grooved region having a plurality of recesses and projections formed thereon such that when the first and second pivotably connected members are in a closed position, the grooved regions of the first and second members are aligned with respect to each other so that the recesses and projections are aligned to form a uniform grooved region. Preferably, the uniform grooved region is formed in an extension on a top surface of the holder assembly so that the grooved region extends above the top surface of the pivotably connected members. Moreover, preferably, the first and second pivotably connected members of the holder assembly may include a locking mechanism for fixedly securing the first member to the second member in a closed position.

The instrument may be configured so that rotation of the vertical drive mechanism vertically moves the rod contacting member with respect to the outer support structure.

Preferably, the surgical instrument is configured so that the holder assembly is removeably attached to the reducing mechanism.

he rod contacting member may be formed as an H-shaped member having a pair of parallel brackets with an intermediate member extending therebetween wherein at least one of the brackets may include a hook sized and configured to engage the spinal rod while the other bracket may include a recess for contacting and biasing the spinal rod into alignment with the U-shaped channel formed in the head of the bone fastener. The second end of the rod contacting member may connect to the outer support structure. The rod contacting member may be pivotably connected to the outer support structure. Alternatively, the second end of the rod contacting member may connect to at least one intermediary support member, which interconnects the rod contacting member with the outer support structure.

Preferably, the intermediary support members may be in the form of a triangular member, wherein the intermediary support members may be fixedly connected to the rod contacting member and pivotably connected to the outer support structure.

The vertical drive mechanism may include a shaft having a first end, a second end, and at least a partially threaded region extending therebetween, wherein the shaft preferably is axially fixed with respect to the outer support structure but rotationally free such that rotation of the shaft causes the holder assembly to move linearly with respect to the outer support structure. More preferably, the shaft may threadably engage the grooved region formed on the holder assembly.

The surgical instrument may also include a horizontal drive mechanism for lateral movement of the spinal rod with respect to the U-shaped channel formed in the head of the bone fastener wherein the horizontal drive mechanism may have a shaft and a lateral support member, the shaft having a first end, a second end, and at least a partially threaded section, the first end of the shaft being connected to the outer support structure, and the lateral support member connecting directly or indirectly to the rod contacting member, wherein the partially threaded section of the shaft interacts with the lateral support member so that operation of the horizontal drive mechanism laterally moves the rod contacting member.

The lateral support member may include a threaded bore extending transversely therethrough for threadably engaging the shaft so that rotation of the shaft moves the lateral support member with respect to the outer support structure to laterally move the rod contacting member.

Preferably, the horizontal drive mechanism may includes a ball-shaped first end for engaging the outer support structure, wherein the ball-shaped first end may be captured within the supporting structure.

Alternatively, the surgical instrument for urging a longitudinal spinal rod into the bone fastener may include a holder assembly, a reducing mechanism, and a horizontal drive mechanism. The holder assembly being sized and configured to engage the bone fastener. The holder assembly comprising a pair of pivotably connected members arranged in a scissor type configuration having a first end and a second end, at least a portion of the first end includes a region having grooves and wherein the second end is sized and configured to engage the head of the bone fastener. The reducing mechanism being sized and configured for moving the spinal rod with respect to the bone fastener. The reducing mechanism comprising a rod contacting member, an outer support structure, and a vertical drive mechanism, the rod contacting member having a first end and a second end, the first end being sized and configured to contact the spinal rod, the outer support structure having a first end, a second end, a drive region, and a holder region wherein the holder region includes a first opening in the first end of the support structure for receiving at least a portion of the first end of the holder assembly and the drive region includes a cavity for receiving at least a portion of the vertical drive mechanism, the vertical drive mechanism including a longitudinal member configured to engage the grooved region of the holder assembly so that movement of the vertical drive mechanism moves the reducing mechanism with respect to the holder assembly in a first direction. The horizontal drive mechanism having a shaft and a lateral support member, the shaft having a first end, a second end, and at least a partially threaded section, the first end of the shaft being connected to the outer support structure, and the lateral support member connecting directly or indirectly to the rod contacting member, wherein the partially threaded section of the shaft interacts with the lateral support member so that operation of the horizontal drive mechanism laterally moves the rod contacting member in a second direction.

BRIEF DESCRIPTION OF THE DRAWINGS

To facilitate an understanding of and for the purpose of illustrating the present invention, exemplary and preferred features and embodiments are disclosed in the accompanying drawings, it being understood, however, that the invention is not limited to the precise arrangements and instrumentalities shown, and wherein similar reference characters denote similar elements throughout the several views, and wherein:

FIG. 3b is a bottom view of the holder assembly shown in FIG. 3a;

FIG. 3c is a side view of the holder assembly shown in FIG. 3a;

FIG. 3d is a top view of the holder assembly shown in FIG. 3a;

FIG. 6b is a side view of the rod contacting member shown in FIG. 6a;

DETAILED DESCRIPTION

For the purposes of promoting an understanding of the principles of the invention, reference will now be made to an exemplary, non-limiting embodiment illustrated in the figures and specific language will be used to describe the same. It will nevertheless be understood that no limitation of the scope of the invention is hereby intended, such alterations and further modifications, and such further applications of the principles of the invention as illustrated herein being contemplated as would normally occur to one skilled in the art to which the invention relates. In this regard, exemplary features may be shown and described which are not required to carry out the invention and thus it is intended that the invention only be limited by the claims.

Figure 1:
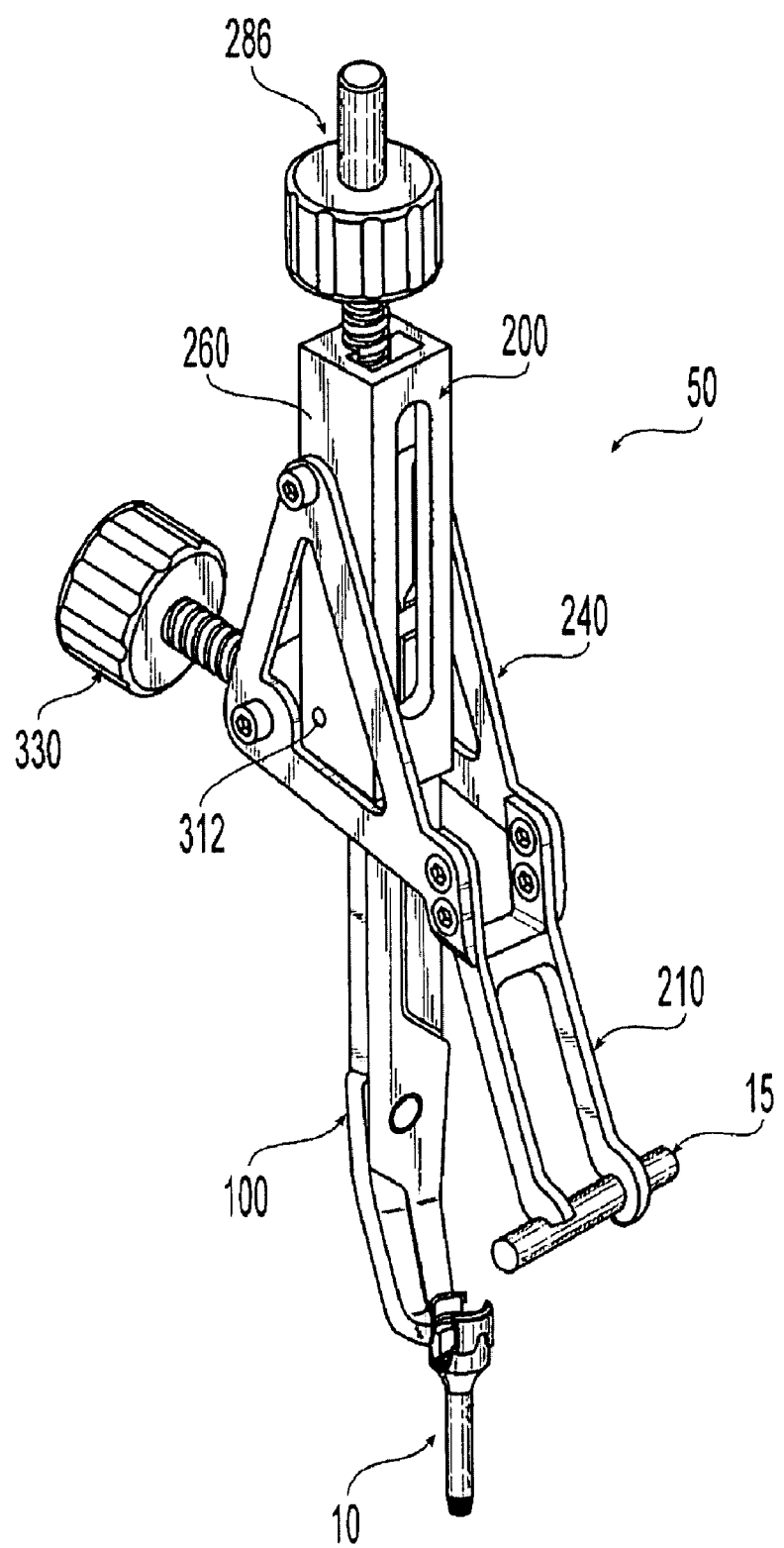
FIG. 1 is a perspective view of a spinal rod insertion instrument engaging a bone fastener and a spinal rod according to one embodiment of the present invention.

As shown in FIG. 1, the spinal rod insertion instrument 50 is a surgical instrument used by surgeons to urge a longitudinal spinal rod 15 into a vertebra engaging spinal implant 10, such as a pedicle screw, a pedicle hook, a transverse process hook, a sublaminar hook, etc. (herein below, referred to generically as a "bone fastener"). It is contemplated that the spinal rod insertion instrument 50 may be used in conjunction with any bone fastener 10 so long as the bone fastener 10 incorporates a rod receiving channel sized and configured to receive a longitudinal spinal rod 15. It is contemplated that the spinal rod 15 can have various cross-sectional shapes, for example, circular, and may or may not be threaded.

Figure 2:
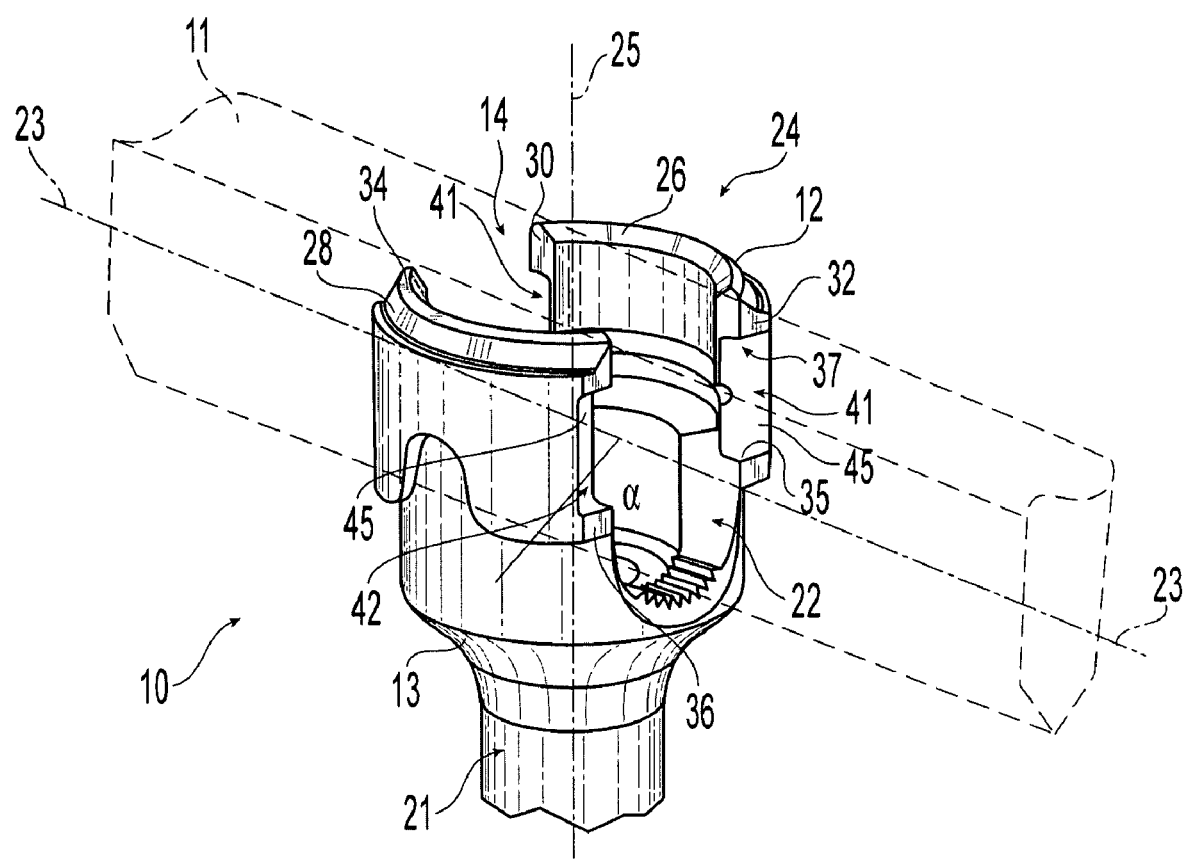
FIG. 2 is a partial view of a bone fastener.

Preferably, as shown in FIG. 2, the bone fastener 10 includes, inter alia, a head 24, which defines a central axis 25, and a bone engaging element 21. The head 24 may further include a top surface 12, a bottom surface 13 and two lateral side walls 26, 28 defining a U-shaped channel 22 and a top opening 14, the top opening 14 communicating with the top of the U-shaped channel 22. The U-shaped channel 22 defines a longitudinal axis 23 normal to the central axis 25. The U-shaped channel 22 being sized and configured for receiving the longitudinal spinal rod 15. The spinal rod 15 preferably being introduced through the top opening 14 for top-loading of the U-shaped channel 22. As shown, the U-shaped channel 22 and top opening 14 thereby define a passageway 11 for the spinal rod 15. The passageway 11 having a substantially U-shaped volume through which the spinal rod 15 may move prior to being fixed in the U-shaped channel 22.

The internal surfaces of the side walls 26, 28 may include an internal thread (not shown), preferably a buttress thread as is well known in the art, for engaging a threaded closure cap (not shown) for retaining the spinal rod 15 in the U-shaped channel 22. However, other closure structures are contemplated including, but not limited, to an internally threaded set screw for engaging external threads formed on the U-shaped channel, an internal/external cam lock, a closure cap having a bayonet-type connection, a snap-fit type connection, a ratchet-type connection, etc.

As shown, the side walls 26, 28 of the pedicle screw each include opposing end faces 30, 32 and 34, 36, respectively. The end faces 30, 32, 34, 36 all preferably include recesses 41, 42 for engaging the spinal rod insertion instrument 50, as will be described in greater detail below. The end faces 30, 32, 34 and 36 may form an angle with respect to the longitudinal axis 23 of the spinal rod 15 of about 85° to about 95° and preferably about 90°. Recesses 41, 42 may include a seat 45 cut out of or chamfered from the end faces 30, 32, 34, 36, the seat 45 being sized and configured to directly engage the spinal rod insertion instrument 50, as will be discussed in greater detail below. The seat 45 may be substantially smooth. Alternatively, the seat may be contoured or coated with a surface treatment to more securely engage the spinal rod insertion instrument 50 with the recess 41, 42.

The recesses 41, 42 may be configured to communicate with the U-shaped channel 22. That is, the seat 45 may be cut inward toward the U-shaped channel 22, thereby forming an angle α measured with respect to longitudinal axis 23 of the U-shaped channel 22. An exemplary angle α may range from about 15° to about 90°, preferably angle α may range from an angle of about 45° to about 75°, and more preferably range from about 55° to about 60°. As shown, with respect to recess 41, recesses 41, 42 further define end walls 35, 37 with seat 45 disposed therebetween. The end walls 35, 37 may be configured and dimensioned to engage the spinal rod insertion instrument 50, thereby providing additional surface contact between the spinal rod insertion instrument 50 and the bone fastener 10 to secure the bone fastener 10 with respect to the spinal rod insertion instrument 50. Although the bone fastener 10 has been described with recesses 41, 42 having a seat 45 to engage the spinal rod insertion instrument 50, an optional end walls 35, 37 to engage the spinal rod insertion instrument, it is contemplated that other structures such as, for example, pins and corresponding pin holes may also be used to engage the spinal rod insertion instrument 50 to the bone fastener 10.

Although the bone engaging element 21 is generally shown as being integral with the head 24 of the bone fastener 10 and in the form of a threaded shaft or shank 21 for anchoring the bone fastener 10 to bone, it should be noted that other configurations are contemplated including, but not limited to, pedicle screws, pedicle hooks, transverse process hooks, sublaminar hooks, etc. Moreover, it is contemplated that the bone fastener 10 may be in the form of a polyaxial screw/hook wherein the bone engaging element 21 is formed separately from and polyaxially connected to the head 24 of the bone fastener 10, thus allowing surgeons to angularly adjust the head 24 and therein the spinal rod 15 with respect to the bone engaging element 21.

Referring again to FIG. 1, the spinal rod insertion instrument 50 may include a holder assembly 100 for engaging the head 24 of the bone fastener 10 and a reducing mechanism 200 for moving a rod contacting member 210 with respect to the holder assembly 100, and thus, moving the spinal rod 15 with respect to the bone fastener 10.

Figure 3A:
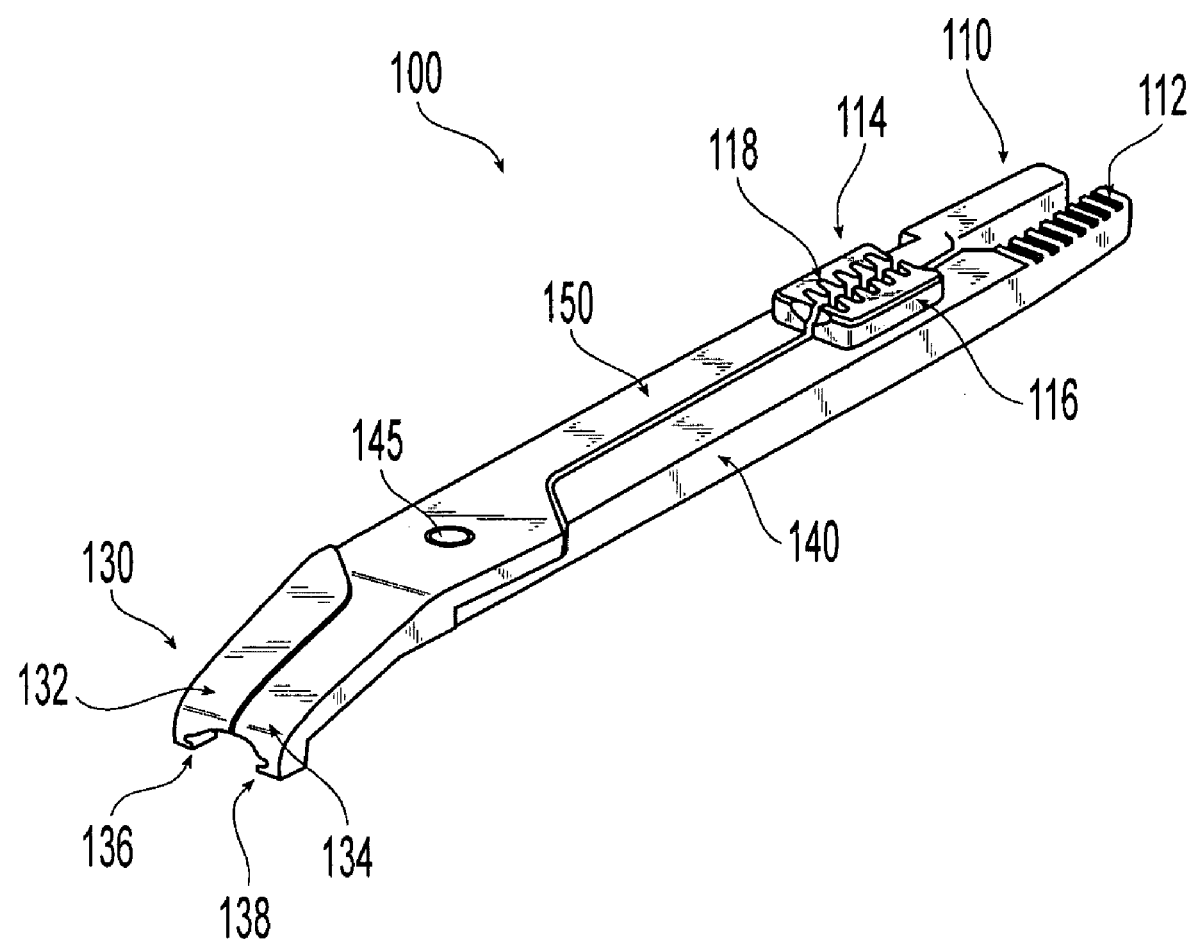
FIG. 3a is a perspective view of the holder assembly of the spinal rod insertion instrument of FIG. 1.
Figure 3B:
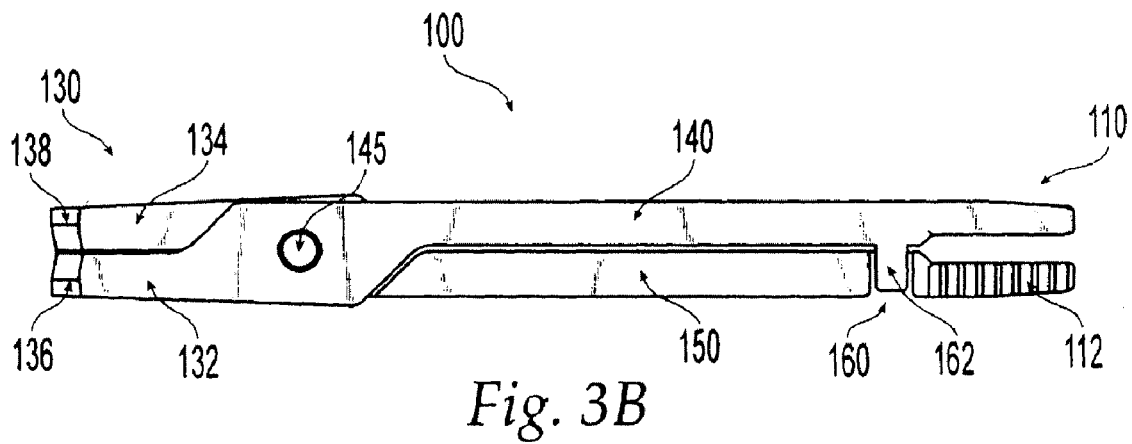
Figure 3C:
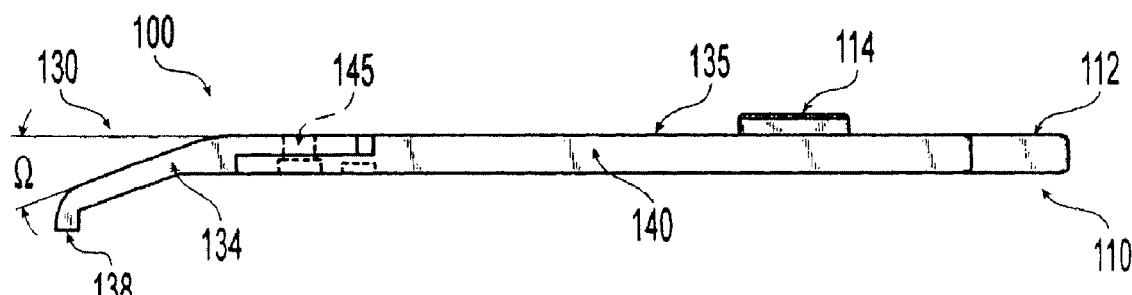
Figure 3D:
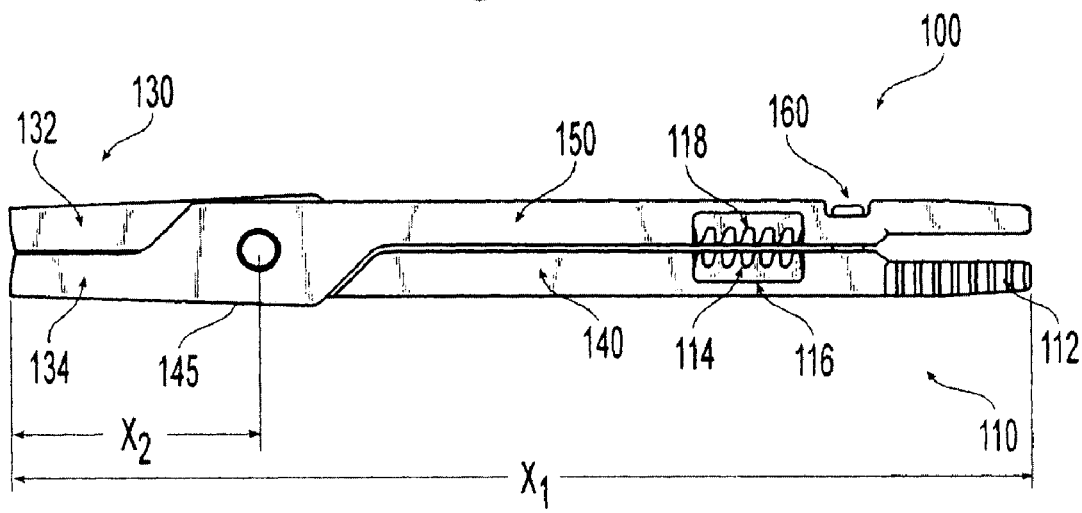

Generally speaking, as best shown in FIGS. 3a-3d, the holder assembly 100 includes a first end 110 and a second end 130, with the second end 130 being sized and configured to securing engage the head 24 of the bone fastener 10. In a preferred embodiment, the holder assembly 100 includes a pair of pivotally connected members 140, 150 having a scissor type arrangement so that movement of the members 140, 150 at the first end 110 causes pivotable corresponding movement of the members 140, 150 at the second end 130 about pivot pin 145. That is, as the surgeon moves the first end 110 of the holder assembly 100 from an opened position (not shown) to a closed position (as shown, for example, in FIG. 3d), the second end 130 of the holder assembly 100 is pivoted about pivot pin 145 from an opened position (not shown) to a closed, i.e., an engaged position (as shown for example, in FIG. 3d). As best shown in FIG. 3d, preferably the holder assembly has an overall length $X_1$, wherein $X_1$ is about 100 millimeters to about 230 millimeters, preferably about 165 millimeters. While the jaws 132, 134 and pivot pin 145 are separated by a distanced $X_2$, wherein $X_2$ is about 25 millimeters to about 60 millimeters, preferably about 40 millimeters.

The second end 130 of the holder assembly 100 may include a pair of jaws 132, 134. The jaws 132, 134 are preferably sized and configured to mate with the head 24 of the bone fastener 10 and, more preferably, sized and configured to engage the side walls 26, 28 of the bone fastener 10. That is, the jaws 132, 134 may include oppositely opposed flats or extensions 136, 138 which are sized and configured to securely engage the recesses 41, 42 formed in the side walls 26, 28 of the bone fastener 10.

Preferably, the extensions 136, 138 are sized and configured to engage the seats 45 formed on the head 24 of the bone fastener 10. Thus creating a tight fit between the jaws 132, 134 and the bone fastener 10 such that the bone fastener 10 is restrained from rotation with respect to the jaws 132, 134. Alternatively, where the bone fastener 10 is already anchored in the patient's bone, the secure engagement of the extensions 136, 138 formed on the jaws 132, 134 with the end walls 35, 37 and the seat 45, prevents the spinal rod insertion instrument 50 from slipping, moving or rotating with respect to the bone fastener 10. Thus, extensions 136, 138 are preferably sized and configured to securely engage the head 24 of the bone fastener 10. It should be noted that if a different structure is formed on the bone fastener 10, such as for example, dimples or pin holes, to engage the spinal rod insertion instrument 50 then the jaws 132, 134 will be configured with different corresponding structure other than the extensions 136, 138 described herein to engage the bone fastener 10.

Figure 4:
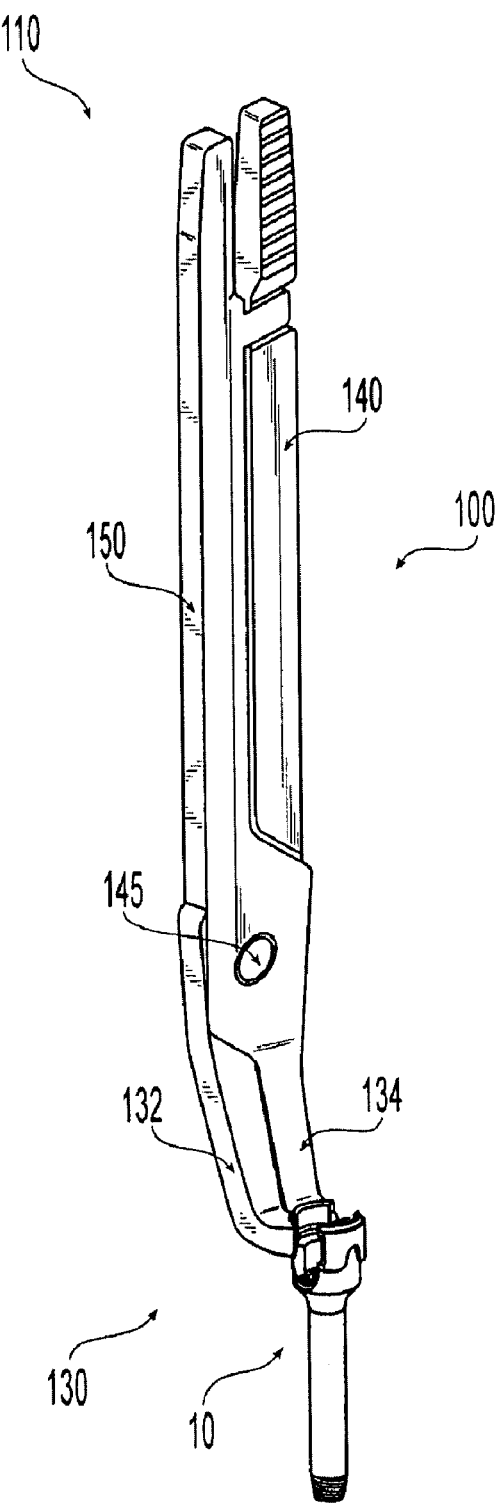
FIG. 4 is a perspective view of the holder assembly shown in FIG. 3a engaging a bone fastener.

As best shown in FIGS. 3c and 4, the holder assembly 100 may be bent by an angle 'Ω so that the jaws 132, 134 and the extensions 136, 138 are out of plane with the first end of the members 140, 150. Preferably, as shown, the jaws are bent by an angle 'Ω of about 24 degrees. In addition, the extensions 136, 138 are preferably sized and configured so that the holder assembly 100 can engage the bone fastener 10 without extending over or interfering with the U-shaped channel 22. The bent shape of the members 140, 150 and the configuration of the jaws 132, 134 and extensions 136, 138 help to avoid interference with the movement of the spinal rod 15 into the U-shaped channel 22. More preferably, lateral engagement of the holder assembly 100 onto the bone fastener 10 such that the jaws 132, 134 engage and contact only one of the sidewalls 26, 28 facilitates introduction of the spinal rod 15 into the U-shaped channel 22 of multiple bone fasteners, which are aligned along the spine where the spinal rod 15 is interconnecting one bone fastener 10 to another bone fastener 10. That is, preferably the holder assembly 100 is sized and configured so that it contacts and engages only the recesses 41 formed on sidewall 26 or only the recesses 42 formed on sidewall 28 so that the spinal rod insertion instrument 50 does not obstruct the passageway 11 and thereby does not interfere with the introduction of the spinal rod 15 into the U-shaped channel 22 when the holder assembly 100 engages the bone fastener 10, as best shown in FIG. 4.

Referring generally to FIGS. 3a-3d and 4, the first end 110 of the holder assembly 100 may include a handle 112 which may have a serrated-type surface for facilitating gripping of the holder assembly 100 by a surgeon. At least a portion of the first end 110 of the holder assembly 100 may also include a region 114 sized and configured for mated engagement with the vertical drive mechanism 275, as will be described in greater detail below. More particularly, as shown, the first and second connecting members 140, 150 may each include a partially threaded region 116, 118 such that when the first and second pivotally connected members 140, 150 are in their closed position, as shown in FIG. 3a, the partially threaded regions 116, 118 are aligned with respect to each other thereby creating a single uniform threaded region 114 for threadedly engaging the vertical drive mechanism 275, as will be described in greater detail below. Preferably, as shown, the at least partially threaded region 114 is formed above and fixedly attached to the holder assembly 100 so that the threaded region 114 extends above the outer surface 135 of the connecting members 140, 150, for reasons which will become apparent below. The threaded region 114 may also be formed integral with and/or within the same plane as the connecting members 140, 150.

Moreover, as best shown in FIG. 3a, the first and second pivotably connected members 140, 150 may also include a locking mechanism 160 which is sized and configured to fixedly secure the first member 140 to the second member 150 in the closed position. The locking mechanism 160 may be any locking mechanism known in the art including, but not limited to, a ratchet type mechanism, a threaded screw and nut type mechanism, etc. Preferably, as shown, the locking mechanism 160 includes a securing arm 162 extending transversely from one of the connecting members 140 towards the other connecting member 150. The securing arm 162 being sized and configured to engage a recess (i.e., an indentation), (not shown) formed in the other connecting member 150 such that when the holder assembly 100 is in the closed position, in which the holder assembly 100 fixedly engages the head 24 of the bone fastener 10, the securing arm 162 may engage the recess to fixedly secure the holder assembly 100 in the closed position. Alternatively, or in addition thereto, the securing arm 162 may have a flange that has a shoulder that contacts the outer surface 135 of the connecting member 150.

Advantageously, the holding assembly 100 may be removeably attachable to the spinal rod insertion instrument 50 so that the holding assembly 100 may be attached to the bone fastener 10 independent of the reducing mechanism 200. In this manner a surgeon can easily manipulate the relatively small and less bulky holding assembly 100 to engage the bone fastener 10. This ability to independently engage the bone fastener 10 is particularly advantageous after the bone fastener 10 has been engaged to the spine and there is limited space in the surgical environment to manipulate the instrument.

Figure 5:
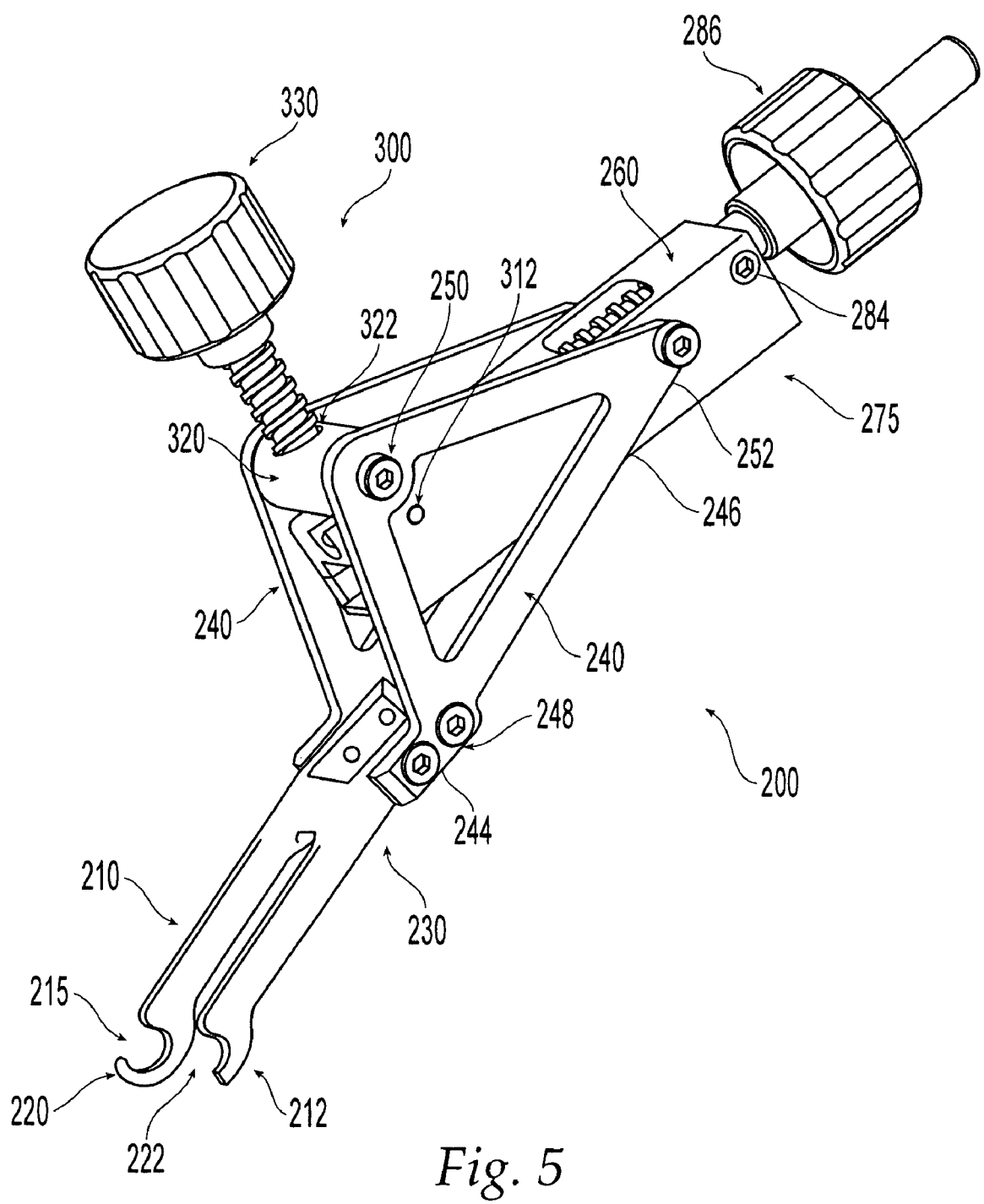
FIG. 5 is a perspective view of the reducing mechanism of the spinal rod insertion instrument of FIG. 1.
Figure 6A:
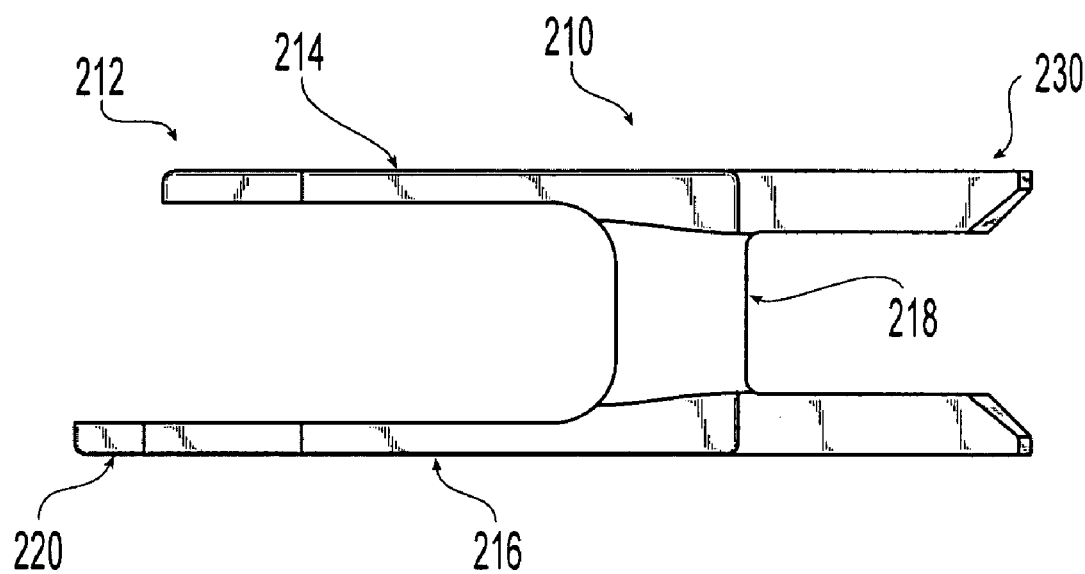
FIG. 6a is a top view of the rod contacting member.
Figure 6B:
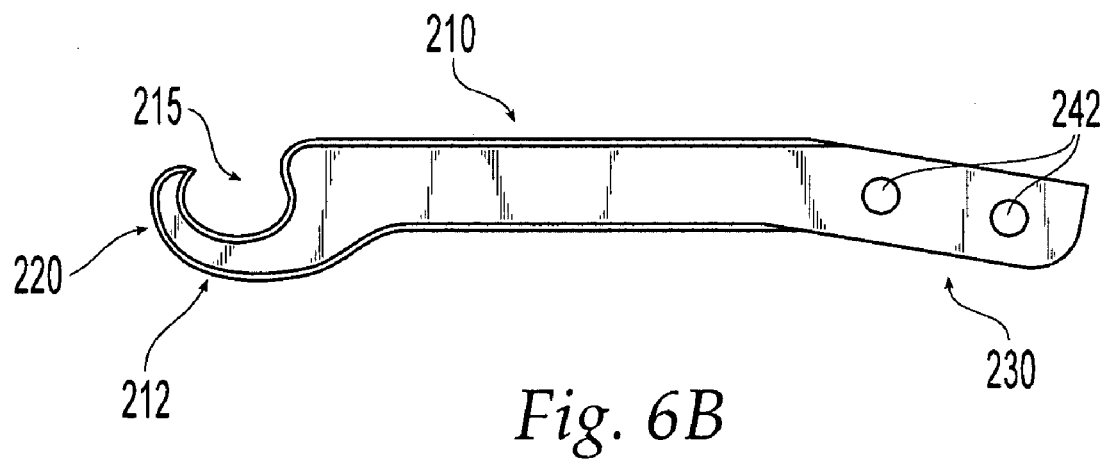

Referring to FIG. 5, the reducing mechanism 200 may include a rod contacting member 210, a vertical drive mechanism 275, and a horizontal drive mechanism 300. As best shown in FIGS. 6a and 6b, the rod contacting member 210 has a first end 212 and a second end 230, the first end 212 being sized and configured to contact the spinal rod 15.

The rod contacting member 210 may generally be in the form of an H-shaped member having a pair of parallel brackets 214, 216 with an intermediate member 218 extending therebetween. Although the rod contacting member 210 has been shown and is described as generally being an H-shaped member, it is contemplated that other shapes and sizes may be used. At least one of the brackets 214, 216 may include a hook 220 sized and configured to have an opening 215 to receive the spinal rod 15 so that the spinal rod 15 may be gripped by the rod contacting member 210. Preferably, one of the brackets 216 contains a hook 220 for gripping the spinal rod 15 while the other bracket 214 contains a recess and/or notch 222 for contacting and biasing the spinal rod 15 into alignment with the U-shaped channel 22 formed in the head 24 of the bone fastener 10. The utilization of a hook 220 and a recess 222 permits a surgeon to more easier engage and disengage the spinal rod 15, as necessary, while still maintaining a secure connection between the rod contacting member 210 and the spinal rod 15. Alternatively, however, the rod contacting member 210 may include a pair of hooks 220 or a pair of recesses 222.

The second end 230 of the rod contacting member 210 may be sized and configured to engage the remaining portions of the reducing mechanism 200. As shown, each bracket 214, 216 of the rod contacting member 210 may engage an intermediary support member 240, which interconnects the rod contacting member 210 with the remaining portions of the reducing mechanism 200. The rod contacting member 210 may connect with the intermediary members 240 by any mechanism known in the art including, but not limited to, screwing, bolting, welding, bonding, pressure fit, etc. Preferably, as shown, the rod contacting member 210 has a pair of holes 242 for receiving a screw and/or rivet 244 for engaging the intermediary members 240 so that the rod contacting member 210 is fixedly secured to the intermediary members 240, and can not pivot with respect thereto. Alternatively, the rod contacting member 210 may connect to the remaining portions of the reducing mechanism 200 by any means known in the art. While the rod contacting member 210 has been shown and described as a component separate from the intermediary support member, and connected thereto, it is contemplated that the rod contacting member 210 and the intermediary support member 240 may be integrally formed.

Figure 7:
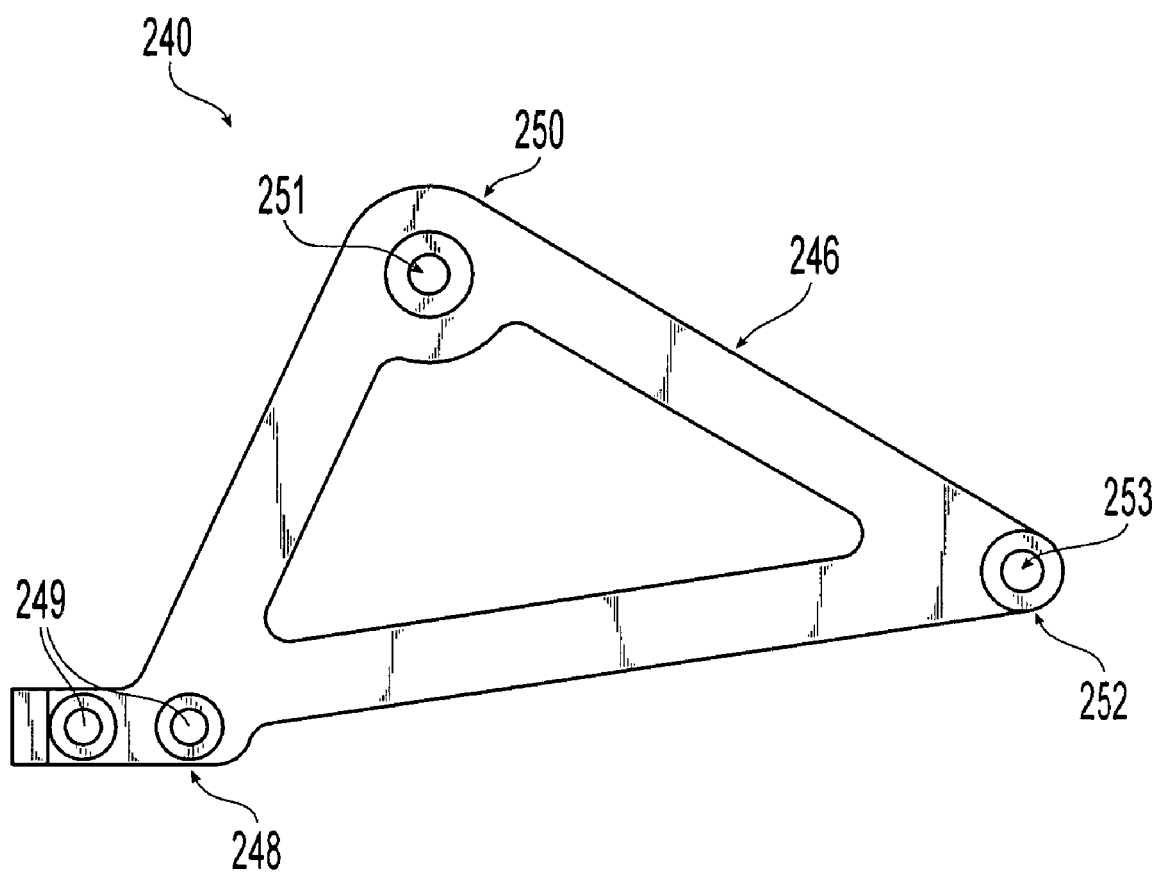
FIG. 7 is a side view of the intermediary support member.

As best shown in FIG. 5, the two intermediary support members 240 preferably are in the form of a triangular 246, one located on either side of the rod contacting member 210. As best shown in FIG. 7, the triangular members 246 have three corners 248, 250, 252 with corner 248 having a pair of screw holes 249 for engaging the rod contacting member 210, while corners 250 and 252 each have a single screw hole 251 and 253, respectively, for pivotally engaging the horizontal drive mechanism 300 and the vertical drive mechanism 275, respectively. Although the intermediary support members 240 have been shown and are described as generally being a triangular member, it is contemplated that other shapes and sizes may be used.

Figure 8:
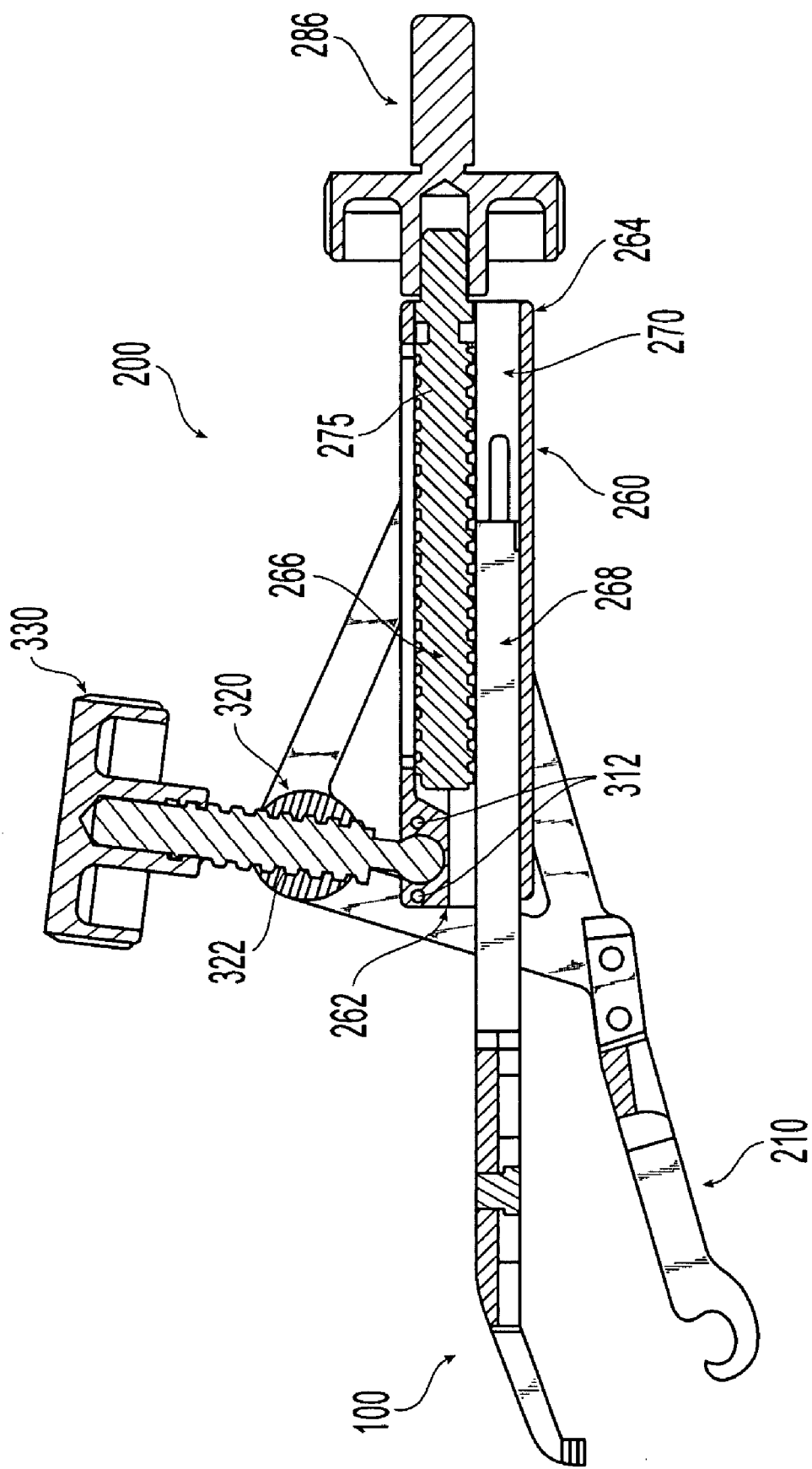
FIG. 8 is a side view, shown in section, of the spinal rod insertion instrument shown in FIG. 1.

Referring to FIGS. 5 and 8, the reducing mechanism 200 may also include an outer support structure 260. The support structure 260 may be pivotally connected to the intermediary members 240 at corner 252 by a screw or pin member which is inserted through hole 253 and connected to support structure 260. The support structure 260, which is shown as being generally rectangular, includes a first end 262, a second end 264, a drive region 266, and a holder region 268. The holder region 268 of the support structure 260 may include a throughbore 270 extending from the first end 262 to the second end 264. The throughbore 270 being sized and configured to engage the holder assembly 100 when the holder assembly 100 is in the closed position. The drive region 266 of the supporting structure 260 is sized and configured to receive a vertical drive mechanism 275. Although the outer support structure 260 has been shown and described as generally being a rectangular member, it is contemplated that other shapes and sizes may be used.

Figure 9:
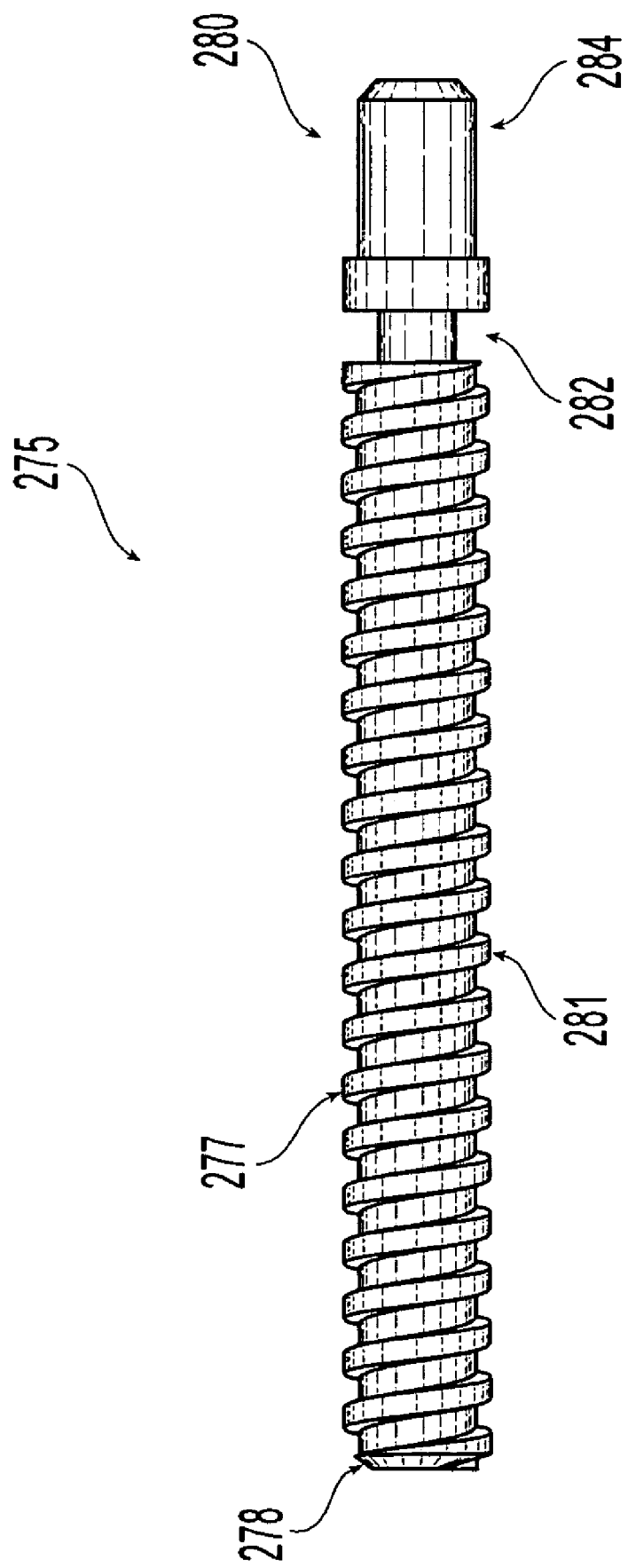
FIG. 9 is a side view of the horizontal drive mechanism.

As shown in FIG. 9, the vertical drive mechanism 275 may be in the form of a longitudinal elongated member, preferably a shaft 277 having a first end 278, a second end 280, and at least a partially threaded region 281 extending therebetween. The partially threaded region 281 may be any mechanism known in the art for permitting translational movement of one member with respect to a second member as a result of the rotational movement of one of the two members. The partially threaded region 281 is preferably sized and configured so that the holder assembly 100 is moved with respect to the vertical drive mechanism 275 as the vertical mechanism 275 is rotated by a surgeon, as will be described in greater detail below. The threaded region 281 may be in the form of a conventional thread, a grooved region, a rack and pinion, a worm gear, etc. Preferably, the partially threaded region 281 is an Acme, ISO trapezoidal screw thread which is sized and configured to transfer load and/or force.

The second end 280 of the shaft 277 preferably includes a reduced diameter recess 282 for mating with at least one screw 284 (as shown in FIG. 5) which extends through the support member 260 such that the vertical drive mechanism 275 is axially fixed with respect to the support structure 260 but rotationally free. Therein, as described in greater detail below, rotation of the vertical drive mechanism 275 causes the holder assembly 100 to move with respect to the support structure 260 as a result of the threaded engagement between the partially threaded region 281 of shaft 277 and the threaded region 114 formed on the holder assembly 100.

The second end 280 of the shaft 277 may also include an engagement portion 284 for securely engaging a knob 286 in order to better facilitate handling and rotation of the vertical drive mechanism 275. The knob 286 being secured to the second end 280 of the shaft 275 by any means known in the art including, but not limited to, a pin, a screw, a rivet, welding, bonding, pressure fit, etc. Alternatively, the second end 280 of the shaft 277 may be sized and configured to engage a drive mechanism, for example, a screwdriver, a hex-driver, a socket, a power tool, etc., or may be sized and configured to be directly engageable by a surgeon.

The spinal rod insertion instrument 50 as shown may operate as follows. Bone fastener 10 is affixed to a patient's bone, preferably the pedicle of a vertebral bone. The spinal rod insertion instrument 50 may thereafter be attached to the bone fastener 10. More specifically, the holder assembly 100 may be attached to the bone fastener 10 by a surgeon manipulating the connecting members 140, 150 so that the jaws 132, 134 formed on the second end 130 of the holder assembly 100 engage the recesses 41, 42 formed on the side walls 26, 28 of the head 24 of the bone fastener 10 as previously described. The holder assembly 100 may thereafter be locked in the closed, i.e., the engaged position by the locking mechanism 160 so that the pivotable connecting members 140, 150 of the holder assembly 100 are closed with respect to each other, the bone fastener 10 is securely held by the holder assembly 100 and the connecting members 140, 150 are locked and thus unable to release the bone fastener 10. Thereafter, the surgeon moves the first end 110 of the holder assembly 100 into the throughbore 270 formed in the holder region 268 of the support structure 260 until the threaded region 114 formed on the holder assembly 100 engages the partially threaded region 281 formed on shaft 277. The vertical drive mechanism 275 may thereafter be rotated, for example, in a counterclockwise direction, which causes the holder assembly 100 to move further into the throughbore 270 formed in the holder region 268 of support structure 260 by the interaction of the partially threaded region 281 formed on shaft 277 and the threaded region 114 of the holder assembly 100. Thereafter, the spinal rod 15, which has been laid adjacent to the bone fasteners 10, is gripped by the rod contacting member 210 so that rotation of the vertical drive mechanism 275, for example, in the clockwise direction causes the shaft 277 to rotate within the drive region 266 of the supporting structure 260, which in turn causes the partially threaded region 281 of shaft 277 to threadedly engage the threaded region 114 of the holder assembly 100. Resulting in the linear and longitudinal movement of the supporting structure 260 with respect to the holder assembly 100, and thus, movement of the spinal rod 15, which is indirectly connected to the supporting structure 260, with respect to the bone fastener 10, which is connected to the holder assembly 100. In this manner, the spinal rod 15 may be moved into the U-shaped channel 22 formed in the head 24 of the bone fastener 10. The spinal rod 15 may thereafter be fixed in the U-shaped channel 22 by a closure cap.

Figure 10:
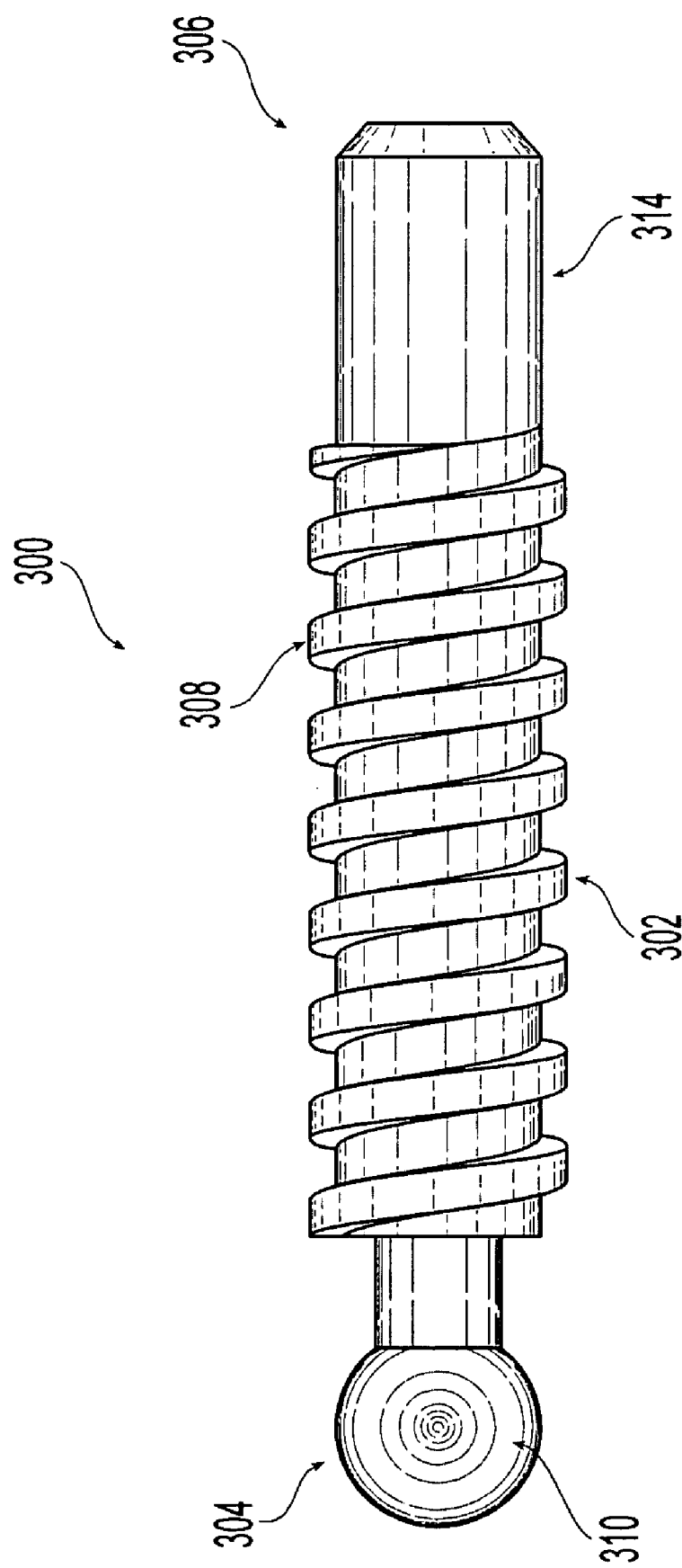
FIG. 10 is a side view of the vertical drive mechanism.

Additionally, the spinal rod insertion instrument 50 may include a horizontal drive mechanism 300 for moving spinal rods 15 that are offset, with respect to the U-shaped channels 22, laterally so that they become vertically aligned with the U-shaped channel 22. As best shown in FIG. 10, the horizontal drive mechanism 300 may be in the form of a longitudinal elongated member, preferably a shaft 302 having a first end 304, a second end 306, and at least a partially threaded section 308 extending therebetween. The partially threaded section 308 may be any mechanism known in the art for permitting translational movement of one member with respect to a second member as a result of the rotational movement of one of the two members. The partially threaded section 308 is preferably sized and configured so that the outer support structure 260 is moved with respect to a lateral support member 320 as the horizontal drive mechanism 300 is rotated by a surgeon, as will be described in greater detail below. The threaded section 308 may be in the form of a conventional thread, a grooved region, a rack and pinion, a worm gear, etc. Preferably, the partially threaded section 308 is an Acme, ISO trapezoidal screw thread which is sized and configured to transfer load and/or force.

The partially threaded section 308 is preferably sized and configured to be retained in a bore 322 formed in a lateral support member 320. The lateral support member 320 preferably is positioned between the pair of intermediary support members 240, as best shown in FIG. 5. The lateral support member 320 may be connected to the intermediary members 240 by any mechanism known in the art including, but not limited to screwing, riveting, welding, bonding, pressure fit, etc.

The lateral support member 320, which is shown as being in the form of a generally cylindrical member, preferably includes a threaded bore 322 (best shown in FIG. 8) extending transversely therethrough for threadedly engaging the partially threaded section 308 of shaft 302. As will be described in greater detail below, the first end 304 of shaft 302 is connected to the supporting structure 260 so that rotation of the horizontal drive mechanism 300 moves the lateral support member 320, and hence the corner 250 of the intermediary support members 240, laterally away from the supporting structure 260. Laterally moving the support structure 260, holder assembly 100 and hence the bone fastener 10, which are directly/indirectly connected together, with respect to the intermediary support members 240, rod contacting member 210, and hence the spinal rod 15, which are directly/indirectly connected together, may align a laterally offset spinal rod 15 with the U-shaped channel 22 formed in the head 24 of a bone fastener 10.

The horizontal drive mechanism 300 preferably includes a ball-shaped first end 310 for engaging the supporting structure 260. Preferably, the ball-shaped first end 310 is secured in a slot (not shown) in the first end 262 of the supporting structure 260 by at least one pin 312, and preferably a pair of pins 312, extending through the supporting structure 260 on the lateral side of the ball-shaped first end 310 so that the horizontal drive mechanism 300 is secured to the supporting member 260 but pivotably connected thereto so that shaft 302 can angulate as the lateral support member 320 moves along the shaft 302 as a result of rotating the horizontal drive mechanism 300.

Similar to the vertical drive mechanism 275, the second end 306 of the horizontal drive mechanism 300 may include an engagement portion 314 for securely engaging a knob 330 in order to better facilitate handling and rotation of the horizontal drive mechanism 300. The knob 330 may be secured to the second end 306 of the shaft 302 by any means known in the art including, but not limited to, a pin, a screw, a rivet, welding, bonding, pressure fit, etc. Alternatively, the second end 306 of the shaft 302 may be sized and configured to engage a drive mechanism, for example, a screwdriver, a hex-driver, a socket, a power tool, etc., or may be sized and configured to be directly engageable by a surgeon.

In one method of use, once the bone fastener 10 has been securely engaged to a patient's vertebra, the longitudinal spinal rod 15 may be aligned with and introduced into the U-shaped channel 22 formed in the head 24 of the bone fastener 10 by use of the spinal rod insertion instrument 50 as follows. The holder assembly 100 may be first attached to the bone fastener 10, more specifically, the jaws 132, 134 formed on the second end 130 of the holder assembly 100 may engage the recesses 41, 42 formed on the side walls 26, 28 of the head 24 of the bone fastener 10, as previously described, or the jaws 132, 134 may be attached in some other manner or through some different structure to the bone fastener 10. The holder assembly 100 may thereafter be locked in the closed, i.e., the engaged position by the locking mechanism 160 so that the pivotable connecting members 140, 150 of the holder assembly 100 are closed with respect to each other and the bone fastener 10 is securely held by the holder assembly 100. Thereafter, the surgeon moves the first end 110 of the holder assembly 100 into the throughbore 270 formed in the holder region 268 of the support structure 260 until the threaded region 114 formed on the holder assembly 100 engages the partially threaded section 281 of shaft 277. The vertical drive mechanism 275 may thereafter be rotated, for example, in a counterclockwise direction, which causes the holder assembly 100 to move further into the throughbore 270 formed in the holder region 268 of support structure 260. Thereafter, the spinal rod 15, which may be positioned adjacent to the bone fasteners 10, may be engaged by the rod contacting member 210. The surgeon may than rotate the horizontal drive mechanism 300 to move the spinal rod 15 laterally in order to vertically align the spinal rod 15 above the top opening 14 of the bone fastener 10 and into alignment with the U-shaped channel 22. More specifically, the horizontal drive mechanism 300 is operated by rotating knob 330, which in turn rotates shaft 302. The partially threaded section 308 formed on shaft 302 interacts with the internally threaded bore 322 formed in the lateral support member 320 along the length of the shaft 302. As the lateral support member 320 moves along the shaft 302, the lateral support member 320 moves the intermediary support members 240 so that they pivot with respect to the supporting structure 260 which, in turn, moves the rod contacting member 210, which laterally moves and repositions the spinal rod 15. In this manner, a laterally offset spinal rod 15 may be aligned with the U-shaped channel 22 formed in the head 24 of the bone fastener 10.

Thereafter, rotation of the vertical drive mechanism 275 will cause the shaft 277 of the vertical drive mechanism 275 to threadedly engage the threaded region 114 of the holder assembly 100. Resulting in vertical movement of the supporting structure 260 with respect to the holder assembly 100, and thus, vertically move the spinal rod 15, which is indirectly connected to the supporting structure 260, into the U-shaped channel 22 formed in the bone fastener 10. The spinal rod 15 may thereafter be fixed in the U-shaped channel 22 by a closure cap.

The present invention has been described in connection with the preferred embodiments. These embodiments, however, are merely for example and the invention is not restricted thereto or limited thereby. Thus, it will be understood by those skilled in the art that other variations and modifications can easily be made within the scope of the invention as defined by the appended claims, thus it is only intended that the present invention be limited by the following claims.

We claim:

1. A surgical instrument for urging a longitudinal spinal rod into a bone fastener, the fastener including a head and a bone engaging portion, the head including a bottom surface, two lateral side walls defining a U-shaped channel, and a top opening, each of the lateral side walls including opposing end faces having a recess formed therein, each of the recesses including a pair of end walls and a seat disposed therebetween, each of the seats being in communication with the U-shaped channel, the instrument comprising:
   a holder assembly for engaging the bone fastener, the holder assembly comprising a pair of pivotably connected members arranged in a scissor type configuration having a first end and a second end, at least a portion of the first end includes a region having grooves and wherein the second end is sized and configured to engage the head of the bone fastener, the second end of the holder assembly including a pair of jaws each having an extension formed thereon for engaging the recesses formed on the lateral side walls of the bone fastener so that the holder assembly can engage the bone fastener without extending over the U-shaped channel, the extensions being sized and configured to engage the seats formed on the head of the bone fastener;
   a reducing mechanism for moving the spinal rod with respect to the bone fastener, the reducing mechanism comprising a rod contacting member, an outer support structure, and a vertical drive mechanism, the rod contacting member having a first end and a second end, the first end being sized and configured to contact the spinal rod, the outer support structure having a first end, a second end, a drive region, and a holder region wherein the holder region includes a first opening in the first end of the support structure for receiving at least a portion of the first end of the holder assembly and the drive region includes a cavity for receiving at least a portion of the vertical drive mechanism, the vertical drive mechanism including a longitudinal member configured to engage the grooved region of the holder assembly so that movement of the vertical drive mechanism moves the reducing mechanism with respect to the holder assembly in a first direction; and
   a horizontal drive mechanism having a shaft and a lateral support member, the shaft having a first end, a second end, and at least a partially threaded section, the first end of the shaft being connected to the outer support structure, and the lateral support member connecting directly or indirectly to the rod contacting member, wherein the partially threaded section of the shaft interacts with the lateral support member so that operation of the horizontal drive mechanism laterally moves the rod contacting member in a second direction;
   wherein the rod contacting member is an H-shaped member incorporating a pair of parallel brackets, one of the brackets including a hook on an end thereof, the hook being sized and configured to engage the spinal rod, the other bracket including a recess formed on an end thereof, the recess being sized and configured to contact the spinal rod, the recess being different than the hook; and
   wherein the second end of the rod contacting member connects to a pair of intermediary support members, each of the intermediary support members being in the form of a triangular member having a first, second and third corner, wherein the first corner is fixedly connected to the rod contacting member, the second corner is pivotably connected to the outer support structure and the third corner is connected to the horizontal drive mechanism.

2. The instrument of claim 1, wherein the grooved region includes a plurality of recesses and projections, and the longitudinal member is at least partially threaded, the threads being sized and configured to interact with the recesses and projections.

3. The instrument of claim 1, wherein rotation of the vertical drive mechanism vertically moves the rod contacting member with respect to the outer support structure.

4. The instrument of claim 1, wherein the holder assembly is removeably attached to the reducing mechanism.

5. The instrument of claim 1, wherein the first end of the holder assembly includes a handle for facilitating gripping of the holder assembly by a surgeon.

6. The instrument of claim 1, wherein the first pivotably connected member of the holder assembly includes a grooved region having a plurality of recesses and projections formed thereon, and the second pivotably connected member includes a grooved region having a plurality of recesses and projections formed thereon such that when the first and second pivotably connected members are in a closed position, the grooved regions of the first and second members are aligned with respect to each other so that the recesses and projections are aligned to form a uniform grooved region.

7. The instrument of claim 6, wherein the uniform grooved region is formed in an extension on a top surface of the holder assembly so that the grooved region extends above the top surface of the pivotably connected members.

8. The instrument of claim 1, wherein the first and second pivotably connected members of the holder assembly include a locking mechanism for fixedly securing the first member to the second member in a closed position.

9. The instrument of claim 8, wherein the locking mechanism includes a securing arm extending transversely from one of the pivotably connected member towards the other pivotably connecting member to engage a recess formed therein.

10. The instrument of claim 8, wherein the locking mechanism includes a securing arm having a shoulder sized and configured to engage a lateral edge.

11. The instrument of claim 1, wherein the vertical drive mechanism includes a shaft having a first end, a second end, and at least a partially threaded region extending therebetween.

12. The instrument of claim 11, wherein the shaft is axially fixed with respect to the outer support structure but rotationally free such that rotation of the shaft causes the holder assembly to move linearly with respect to the outer support structure.

13. The instrument of claim 12, wherein the shaft threadably engages the grooved region formed on the holder assembly.

14. The instrument of claim 1, wherein the lateral support member has a threaded bore extending transversely therethrough for threadably engaging the shaft so that rotation of the shaft moves the lateral support member with respect to the outer support structure to laterally move the rod contacting member.

15. The instrument of claim 14, wherein the horizontal drive mechanism includes a ball-shaped first end for engaging the outer support structure.

16. The instrument of claim 15, wherein the ball-shaped first end is captured within the supporting structure.

17. The instrument of claim 16, wherein the ball-shaped first end is captured within the supporting structure by a pair of pins extending through the supporting structure.

18. The instrument of claim 17, wherein the second end of the shaft includes an engagement portion for securely engaging a knob.

* * * * *